US00PP26354P3

(12) United States Plant Patent

Klemm et al.

(10) Patent No.: US PP26,354 P3

(45) Date of Patent: Jan. 26, 2016

(54) *PETUNIA* PLANT NAMED 'KLEPH13227'

(50) Latin Name: *Petunia hybrida*
Varietal Denomination: KLEPH13227

(71) Applicant: Klemm+Sohn GmbH & Co. KG, Stuttgart (DE)

(72) Inventors: Nils Klemm, Stuttgart (DE); Antonella Capo, Latina (IT)

(73) Assignee: Klemm+Sohn GmbH & Co. KG, Stuttgart (DE)

( * ) Notice: Subject to any disclaimer, the term of this patent is extended or adjusted under 35 U.S.C. 154(b) by 89 days.

(21) Appl. No.: 14/120,063

(22) Filed: Apr. 21, 2014

(65) Prior Publication Data

US 2015/0305220 P1 Oct. 22, 2015

(51) Int. Cl.
*A01H 5/02* (2006.01)

(52) U.S. Cl.
USPC ..... Plt./356.21

(58) Field of Classification Search
USPC ..... Plt./356.21, 356.1
See application file for complete search history.

*Primary Examiner* — Susan McCormick Ewoldt

(74) *Attorney, Agent, or Firm* — James M. Weatherly; Bethany R. Roahrig; Cochran Freund & Young, LLC

(57) ABSTRACT

A new *Petunia* plant particularly distinguished by having single, salmon colored flowers with a pronounced vein, medium, compact plant form and an upright, mounding plant habit, is disclosed.

1 Drawing Sheet

Genus and species: *Petunia hybrida.*
Variety denomination: 'KLEPH13227'.

BACKGROUND OF THE NEW PLANT

The present invention comprises a new and distinct variety of *Petunia*, botanically known as *Petunia hybrida* and hereinafter referred to by the variety name 'KLEPH13227'. 'KLEPH13227' is a selection from a cross-pollination of the proprietary female *Petunia* line 'PH-2008-0218' (unpatented) and the proprietary male *Petunia* line 'PH-2002-V 133' (unpatented).

In July of 2009 the proprietary female *Petunia* line 'PH-2008-0218' and the proprietary male *Petunia* line 'PH-2002-V 133' were cross pollinated in Latina, Italy and seeds were obtained. The seeds were sown and plants were grown for evaluation. A plant line was selected in April 2010 in Latina, Italy and named 'KLEPH13227'. In April 2010, 'KLEPH13227' was first vegetatively propagated by terminal tip cuttings and tissue culture. 'KLEPH13227' was found to reproduce true to type in successive generations of asexual propagation via terminal tip cuttings and tissue culture in Stuttgart, Germany and Tenerife, Spain.

SUMMARY

The following are the most outstanding and distinguishing characteristics of this new variety when grown under normal horticultural practices in Stuttgart, Germany and Latina, Italy.

1. Single, salmon colored flowers with a pronounced vein;
2. A medium, compact plant form; and
3. An upright, mounding plant habit.

DESCRIPTION OF THE PHOTOGRAPHS

This new *Petunia* plant is illustrated by the accompanying photographs which show an overall view of the plant. The colors shown are as true as can be reasonably obtained by conventional photographic procedures.

DESCRIPTION OF THE NEW VARIETY

Figure 1:
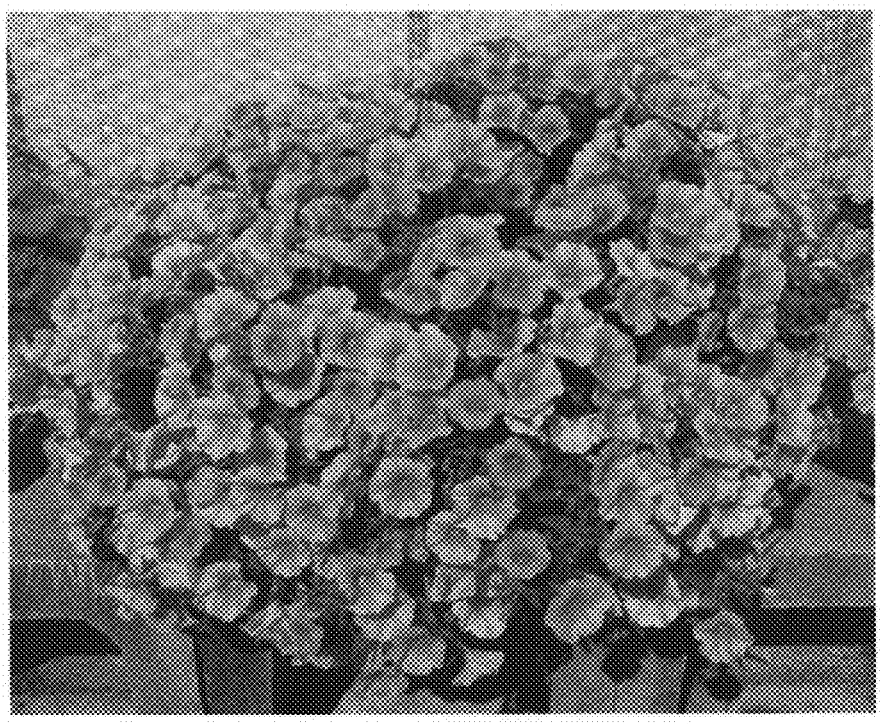
FIG. 1 shows the overall plant habit of the plant grown in a basket. The plant is about 5 months-old grown in Stuttgart, Germany in July 2013.
Figure 2:
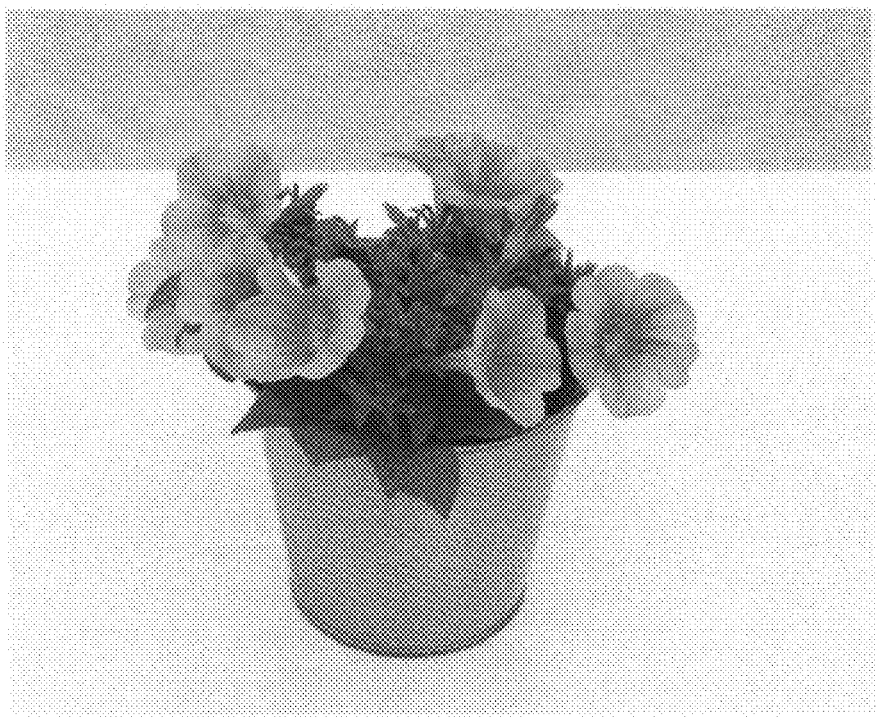
FIG. 2 shows a close-up of the mature inflorescence of the plant grown in a pot. The plant is about 3 months-old grown in Stuttgart, Germany in May 2013.

The following detailed descriptions set forth the distinctive characteristics of 'KLEPH13227'. The data which define these characteristics were collected from asexual reproductions carried out in Latina, Italy. Data was collected on thirteen-week-old plants grown indoors in Latina, Italy under greenhouse conditions in March of 2014. Color references are to The R.H.S. Colour Chart of The Royal Horticultural Society of London (R.H.S.), 5$^{th}$ edition (2007).

Classification:
- *Family.*—Solanaceae.
- *Species.—Petunia hybrida.*
- *Common name.—Petunia.*
- *Variety.*—'KLEPH13227'.

Parentage:
- *Female.*—Proprietary *Petunia* line 'PH-2008-0218'.
- *Male.*—Proprietary *Petunia* line 'PH-2002-V 133'.

Plant:
- *Form.*—Medium, compact.
- *Habit.*—Upright, mounding.
- *Height (from top of soil).*—15.0 cm to 18.0 cm.
- *Width (horizontal plant diameter).*—About 25.0 cm.
- *Propagation.*—Terminal tip cuttings.
- *Time to produce a finished flowering plant.*—13 to 14 weeks in winter, 7 weeks in spring.
- *Time to initiate and develop roots.*—2 to 3 weeks.

*Root description*.—Moderate density, moderate branching, white roots.

Stems:

*Average number* (*basal*).—About 15.0 cm.

*Length of basal branches* (*from the base of the stem to the tip*).—About 12.0 cm.

*Internode length*.—1.3 cm.

*Diameter of branches* (*from midpoint*).—0.3 cm.

*Stem color*.—RHS 144B.

*Anthocyanin*.—Absent.

*Texture*.—Pubescent.

Leaves:

*Arrangement*.—Alternate at the base of the stems, opposite on the flower stems.

*Length*.—About 5.0 cm.

*Width*.—About 2.8 cm.

*Shape*.—Elliptic.

*Apex*.—Broadly acute.

*Base*.—Attenuate.

*Margin*.—Entire.

*Immature leaf color*.—Upper surface: RHS N137B. Lower surface: RHS 138A.

*Mature leaf color*.—Upper surface: RHS N137B. Lower surface: RHS 138A.

*Texture*.—Both upper and lower surfaces: Slightly pubescent.

*Venation pattern*.—Arcuate.

*Venation color*.—Both upper and lower surfaces: RHS 144A.

*Petioles*.—Length: 0.7 cm. Diameter: 0.2 cm. Color: RHS 144B. Texture: Slightly pubescent.

Flower bud:

*Shape*.—Irregular oblong.

*Length*.—About 4.0 cm.

*Diameter*.—0.5 cm to 0.8 cm.

*Color at tight bud*.—RHS 184A.

*Texture*.—Slightly pubescent.

Inflorescence:

*Blooming habit* (*flowering season*).—Permanent flowering during summer time.

*Inflorescence type*.—Cymose.

*Number of flowers per node*.—One.

*Lastingness of individual blooms on the plant*.—About one week.

*Fragrance*.—Weak.

*Flowers*.—Arrangement: Composed of 5 petals fused at the base. Shape: Funnel form. Diameter (flower face): 5.8 cm. Depth (total length of flower): 6.0 cm. Throat/Funnel: Length: 2.5 cm to 3.0 cm. Diameter (at opening): 1.5 cm. Texture: Both inner and outer surfaces: Smooth, glabrous. Color: Creamy white with veins of RHS 53A. Color, immature flower: Face/Margin: RHS 51C. Upper surface: RHS 51B and RHS N34A (vein). Lower surface: RHS 65C. Color, mature flower: Face/Margin color: RHS 62A. Upper surface: RHS 62A and RHS 53A (vein). Lower surface: RHS 63C.

*Petals*.—Color: Inner surface: RHS 62A and RHS 53A (vein). Outer surface: RHS 63C. Apex: Obtuse mucronate. Base: Fused. Margin: Entire. Strength of waviness: Weak. Degree of lobation: Weak.

*Calyx arrangement*.—Actinomorphic, composed of 5 sepals.

*Sepals*.—Color: Upper surface: RHS 137B. Lower surface: RHS 137C. Length: 2.0 cm. Width: 0.4 cm. Shape: Linear. Apex: Acute. Base: Attenuate. Margin: Entire. Texture: Both upper and lower surfaces: Slightly pubescent.

*Pedicels*.—Color: RHS 144A. Length: About 3.0 cm. Diameter: 0.2 cm. Texture: pubescent.

Reproductive organs:

*Stamens*.—Quantity: 5. Shape: Needle with elliptic head. Filament: Length: 1.6 cm. Diameter: 0.05 cm. Color: RHS 36D. Anther: Shape: Elliptic. Color: RHS 158D. Length: 0.2 cm. Diameter: 0.25 cm. Pollen: Color: RHS 11D. Amount: Moderate.

*Pistils*.—Quantity per flower: 1. Length: 1.9 cm. Stigma color: RHS 145A. Style color: RHS 145C.

Fruit and seed set: No fruit and seed set observed to date.

Disease and pest resistance: No disease and pest/insect resistance observed.

COMPARISON WITH PARENTAL LINES AND KNOWN VARIETY

'KLEPH13227' is a distinct variety of *Petunia*. 'KLEPH13227' is distinguished from its parents as described in Table 1:

TABLE 1

Comparison with Parental Lines

| Trait | Variety 'KLEPH13227' | Female parent 'PH-2008-0218' | Male Parent 'PH-2002-V133' |
|---|---|---|---|
| Flower shape | Single flower | Double flower | |
| Flower color | Salmon with vein | Salmon | White |

'KLEPH13227' is most similar to the commercial *Petunia* plant named 'Famous Salmon Pink' (unpatented). Differences between the two varieties are described in Table 2:

TABLE 2

Comparison with Similar Variety

| Trait | Variety 'KLEPH13227' | Commercial line 'Famous Salmon Pink' |
|---|---|---|
| Plant habit | More mounding | Uneven habit with dominant stems |
| Flower color and shape | More pronounced vein | Less pronounced vein, stronger petal lobation than 'KLEPH13227' |

We claim:

1. A new and distinct variety of *Petunia* plant named 'KLEPH13227' as shown illustrated and described herein.

* * * * *